United States Patent
Dooley et al.

(10) Patent No.: US 9,410,911 B2
(45) Date of Patent: Aug. 9, 2016

(54) STRUCTURE AND METHOD OF MANUFACTURE

(71) Applicant: HEWLETT-PACKARD DEVELOPMENT COMPANY, L.P., Houston, TX (US)

(72) Inventors: Kevin Dooley, Wicklow (IE); Richard Coull, Louth (IE); Graeme Scott, Kildare (IE); Lorraine Byrne, Dublin (IE)

(73) Assignee: Hewlett-Packard Development Company, L.P., Houston, TX (US)

( * ) Notice: Subject to any disclaimer, the term of this patent is extended or adjusted under 35 U.S.C. 154(b) by 277 days.

(21) Appl. No.: 13/868,435

(22) Filed: Apr. 23, 2013

(65) Prior Publication Data

US 2014/0314624 A1    Oct. 23, 2014

(51) Int. Cl.
| | |
|---|---|
| *G01N 27/07* | (2006.01) |
| *C25D 5/02* | (2006.01) |
| *G01N 27/04* | (2006.01) |
| *C25D 3/12* | (2006.01) |
| *G01N 27/12* | (2006.01) |
| *B82Y 30/00* | (2011.01) |

(52) U.S. Cl.
CPC ............... *G01N 27/07* (2013.01); *C25D 5/022* (2013.01); *G01N 27/048* (2013.01); *B82Y 30/00* (2013.01); *C25D 3/12* (2013.01); *G01N 27/126* (2013.01); *G01N 27/127* (2013.01)

(58) Field of Classification Search
CPC ... G01N 27/07; G01N 27/048; G01N 27/126; G01N 27/127; C25D 5/022; C25D 3/12; B82Y 30/00
USPC .................................. 438/1, 48, 49, 942–952
See application file for complete search history.

(56) References Cited

U.S. PATENT DOCUMENTS

| | | | |
|---|---|---|---|
| 7,534,470 | B2 | 5/2009 | Madou et al. |
| 8,385,046 | B2 | 2/2013 | Palusinski et al. |
| 2010/0116682 | A1 | 5/2010 | Neuzil et al. |
| 2011/0316054 | A1 | 12/2011 | Fedder et al. |

OTHER PUBLICATIONS

Sander, D., et al. "Fabrication of metallic microstructures by electroplating using deep-etched silicon molds." Microelectromechanical Systems, Journal of 4.2 (1995): 81-86.*
Pan, Li-Wei, and Liwei Lin. "Batch transfer of LIGA microstructures by selective electroplating and bonding." Microelectromechanical Systems, Journal of 10.1 (2001): 25-32.*

(Continued)

*Primary Examiner* — Lyle Alexander
*Assistant Examiner* — Robert Eom
(74) *Attorney, Agent, or Firm* — Mannava & Kang, P.C.

(57) ABSTRACT

A structure for a chemical sensing device, the structure comprising at least one electrically conductive element located in, and protruding from, at least one recess. A method of manufacturing the structure includes: (a) providing a template comprising at least one recess having a recess depth; (b) providing an electrically conductive material in the at least one recess; and (c) removing part of the template to decrease the recess depth of the at least one recess, thereby forming said protruding at least one electrically conductive element.

10 Claims, 5 Drawing Sheets

(56) References Cited

OTHER PUBLICATIONS

Rogner, A., et al. "The LIGA technique-what are the new opportunities." Journal of Micromechanics and Microengineering 2.3 (1992): 133.*

Chamran et al; Fabrication of High-aspect-ratio Electrode Arrays for Three-dimensional Microbatteries; Journal of Microelectromechanical Systems, vol. 16, No. 4, Aug. 2007.

* cited by examiner

STRUCTURE AND METHOD OF MANUFACTURE

BACKGROUND

A chemical sensing device may be used to determine the presence of at least one certain chemical. Such a device may exhibit a known response when exposed to a chemical, allowing the presence of the chemical to be detected.

Known chemical sensing devices comprise sensing materials which exhibit a change in a certain property, for example electrical conductivity, when they come into contact with certain chemicals. The sensitivity of known chemical sensing devices is limited by the detectability of this change upon exposure to such chemicals.

BRIEF DESCRIPTION OF THE DRAWINGS

The accompanying drawings illustrate examples of the principles described herein and are a part of the specification. The illustrated examples are merely examples and do not limit the scope of the claims.

DETAILED DESCRIPTION

In the following description, for purposes of explanation, numerous specific details are set forth in order to provide a thorough understanding of the present apparatus and methods. It will be apparent, however, to one skilled in the art that the present apparatus, systems and methods may be practiced without these specific details. Reference in the specification to "an example" or similar language means that a particular feature, structure, or characteristic described in connection with the example is included in at least that one example, but not necessarily in other examples.

As described above, chemical sensing devices may be used to detect the presence of at least one certain chemical by exploiting a known change in a certain property, for example the electrical conductivity, of a component of the sensing device when exposed to the chemical of interest (which may be referred to as the analyte).

Examples of a structure for a chemical sensing device will now be described. Such structures comprise at least one recess and at least one electrically conductive element located in, and protruding from, the at least one recess.

Figure 1:
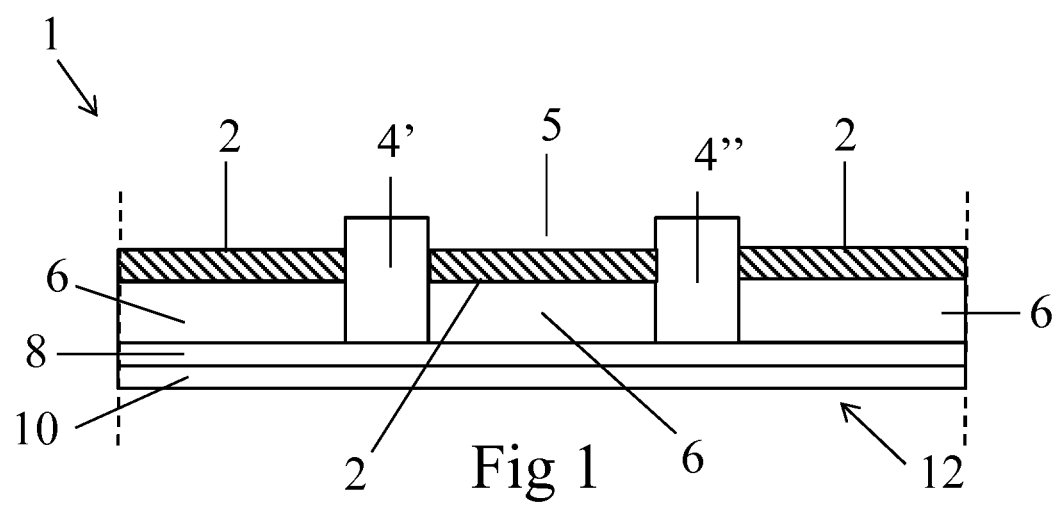
FIG. 1 shows schematically an example of part of a chemical sensing device.

FIG. 1 shows part of an example chemical sensing device 1 comprising a structure 12 which comprises at least one recess and at least one electrically conductive element 4', 4" located in, and protruding from, the at least one recess. Each electrically conductive element is supported by the sides of a recess and by at least one substrate 8, 10 as described in more detail later.

In the example shown in FIG. 1, a first electrically conductive element 4' and a second electrically conductive element 4" are shown; the structure in this example comprises more than two electrically conductive elements; however, for clarity, only two electrically conductive elements are shown. The extent of the structure shown is indicated by the dashed lines, but it is to be appreciated that the extent continues to the left and right of the Figure with further pairs of electrically conductive elements separated by a sensing material. In other examples there may only be two electrically conductive elements. In the present example, the electrically conductive elements are ridges extending along an axis perpendicular the plane of the page of FIG. 1, each ridge having a rectangular cross section. In another example, the electrically conductive elements may form an array of interdigitated elements; in other words, the electrically conductive elements may form a pattern of interlocking, yet electrically isolated, protrusions.

In this example, the first and second electrically conductive elements 4', 4" are separated by an inter-element space 5. A sensing material 2 is provided in the inter-element space 5 so as to at least partially fill the inter-element space 5 and to lie in contact with the first and second electrically conductive elements 4', 4". In this example, the sensing material 2 doesn't cover the electrically conductive elements 4', 4" but, in other examples, the sensing material may cover at least one of the electrically conductive elements and at least partially fill the inter-element space; for example, as a film. The sensing material 2 is chosen such that a certain property of the sensing material 2, for example electrical conductivity, changes upon exposure to an analyte of interest. The sensing material is provided on a material 6 which is supported by the at least one substrate 8, 10 and which fills at least part of the inter-element space 5. The two electrically conductive elements and sensing material may be considered as a resistor, with the resistance depending on the following equation:

$$R = \rho L / A,$$

where R refers to the resistance of the resistor, $\rho$ refers to the resistivity of the sensing material, length L refers to the separation between the two electrically conductive elements, and A refers to the cross-sectional area of the resistor in a direction orthogonal to the length L.

In the example in which the electrical conductivity of the sensing material 2 changes when it is exposed to the analyte, an electrical link, i.e. an electrical connection, is formed between the electrically conductive elements 4', 4" via the sensing material 2. The conductivity of this link changes depending on the chemical environment it is exposed to. For example, if the sensing material 2 is exposed to the analyte of interest, the conductivity of the sensing material will change by a known amount in dependence on the analyte concentration; this change is measurable.

Therefore, by monitoring the electrical properties of the electrical link, such as the resistance or electrical conductivity for example, the presence of the analyte and in some examples also the concentration of the analyte can be determined. For example, if a detected change in resistance across the electrical link is equal to the expected change in resistance upon exposure to the analyte, this indicates that the analyte is present.

The electrical properties of the electrical link may be measured using well-known, commercially available measuring devices, for example an ohmmeter, ammeter and/or voltmeter device or a multimeter such as the Model 2401 Low Voltage SourceMeter available from Keithley Instruments Inc., Western Peninsula Building, Western Road, Bracknell, Berkshire, RG12 1RF, United Kingdom. The measuring device is connected to the electrically conductive elements via electrical connections (not shown). In turn, the measuring device may be connected to a processing system, comprising for example at least one memory and at least one processor, for processing output signals of the measuring device, which output signals are indicative of the electrical property of the electrical link between the elements. The memory may store data, for example in a look up table, indicative of electrical property values, for example electrical conductivity, or a change in electrical conductivity or a rate of change of electrical conductivity, which corresponds with a known concentration of analyte. Thus, a presence and concentration of analyte may be determined based on an electrical conductivity value measured by the measuring device. The processor may also be connected for example to a display, for displaying data indicating that an analyte is present, and/or a concentration of analyte present. A variety of different materials may be used to form the sensing material 2. In addition to the material choice, a porosity of the sensing material to the analyte affects performance of detecting the analyte. The density of the network of the applied sensing material may also need to be above a percolation threshold to the analyte, to enable conductivity between the electrically conductive elements. In an example, the sensing material 2 is selected from the group consisting of: a conductive organic polymer; inorganic nanoparticles coated with metal nanoparticles; inorganic nanoparticles coated with oxide nanoparticles; graphene; carbon nanotubes coated with metal nanoparticles; and carbon black.

More specifically, for example, a conductive organic polymer material such as poly(thiophene)s (PT), poly(3,4-ethylenedioxythiophone (PEDOT) or poly(p-phenylene sulfide) (PPS), available from Sigma Aldrich Ltd., The Old Brickyard, New Road, Gillingham, Dorset, SP8 4XT, UK, may be used for the sensing material 2. Alternatively, the sensing material 2 may comprise inorganic metal or metal oxide nanoparticles, with such metals being for example platinum (Pt), rhodium (Rh), rubidium (Ru), platinum/rubidium (Pt/Ru), or platinum/cobalt metal (Pt/Co) available from Sigma Aldrich Ltd. In a further example, carbon nanotubes, such as type ASP-100F single-walled carbon nanotubes, available from Hanwha Chemical, Hanwha Building, 1 Janggyo-dong, Jung-gu, Seoul, South Korea, or graphene sheets, functionalized, for example coated, with metal nanoparticles, such as nickel, gold or palladium, may also be used; additional functionalization of these nanoparticles with molecular ligands selective to a particular analyte can be achieved through attachment of the ligand via thiol (—SH) functionality in the case of gold (Au) and palladium (Pd) and silane coupling agents in the case of nickel (Ni). The skilled person would readily understand methods for such functionalizing. Graphene sheets may be produced by solution processing graphite flakes, available from Sigma Aldrich Ltd. for example. The metal nanoparticles for functionalization can be deposited by electroless deposition, electrodeposition or vapour deposition chemicals for plating deposition, and may be purchased from Enthone Inc., Worldwide Headquarters, 350 Frontage Road, West Haven, Conn. 06516, USA. In another example, nano wires, such as silver nano wires available from Seashell Technology LLC, 3252 Holiday Ct. #115, La Jolla, Calif. 92037, USA, may be used. Alternatively, carbon black pigment, available from Hewlett-Packard Company, 3000 Hanover Street, Palo Alto, Calif. 94304-1185, USA, may be used; for example a commercially available black inkjet ink comprising carbon black pigment may be used, for inkjet printing the sensing material. The sensitivity of the chemical sensing device may depend on the number of possible electrical connections within the electrical link described above; the number of possible electrical connections may depend on the pigment size of the carbon black, which may be chosen appropriately to provide the desired device sensitivity. In a particular example, carbon black pigment is used to detect the presence of water vapor. The carbon black pigment conducts electricity when dry, and the conductivity predictably changes in the presence of water vapor. Such a chemical sensing device in combination with a temperature measuring device to give temperature data allows an accurate relative humidity measurement to be determined.

In an alternative example, the sensing material 2 is a semiconductor material, so the electrical link functions as a semiconductor. A change in the electrical conductivity of the electrical link may be measured to detect the presence of an analyte.

In the example illustrated in FIG. 1, the chemical sensing device 1 comprises two electrically conductive elements 4', 4" forming a pair of elements for detecting an analyte. The chemical sensing device 1 may comprise more than one pair of electrically conductive elements, to form an array of pairs of elements. Each pair of elements may be electrically linked by the same type of sensing material, or different pairs may be electrically linked by different types of sensing material for detecting different analytes. In each case, the array of elements will be connected to a measuring device and processing system, similar to that described previously, but configured accordingly for an array as the skilled person would readily understand. In the case where each pair of elements in an array is linked by the same type of sensing material, the processing system may be configured to determine an average concentration of analyte present over the entire array. In further examples, there may be a plurality of arrays of elements, with each array forming a region of a larger chemical sensing device, with a plurality of regions, with each region being configured to detect the presence of a different analyte.

Using FIG. 2, the example structure 12 will now be described in more detail. For clarity of illustration, the sensing material is not illustrated in FIG. 2.

Figure 2:
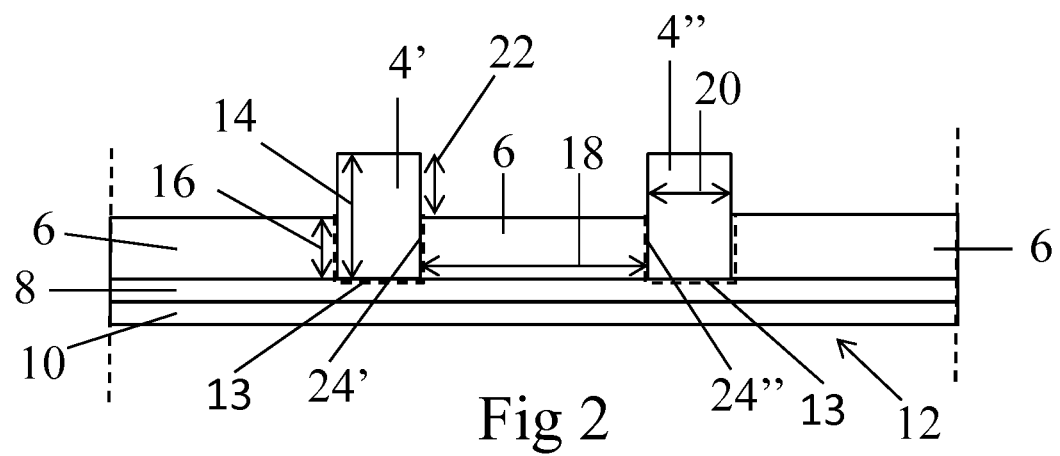
FIG. 2 shows schematically an example of part of a structure for a chemical sensing device.

In the structure 12 of FIG. 2, each of the electrically conductive elements 4', 4" are located in, and protrude from, a recess 13 in the material 6. The recess 13 is schematically indicated by dashed lines in the Figure. It is to be appreciated that the sides of the recess 13 lie in contact with the sides of the electrically conductive elements 4', 4". Within a space between the protruding parts of the electrically conductive elements may be placed a sensing material for sensing analyte of interest.

Each recess is an opening, in other words a hole or a cavity, having a recess depth 16 which defines the extent to which the recess extends into the material in which it is formed. Each recess also has a recess width 20, which is orthogonal to the recess depth 16. The recess width defines a lateral extent of a recess. The example recesses shown in FIG. 2 are rectangular, with a constant recess width and recess depth, however, in other example recesses, the recess width and/or recess depth may change throughout the recess. For example, recesses may have a greater width at the entrance to the recess, and a narrower width at the base of the recess. It is to be noted that each recess extends along an axis lying perpendicular to the plane of the page of FIG. 2. Therefore, in three dimensions, each recess is a channel for example.

The electrically conductive elements 4', 4" located within the recesses 13 have an element length 14, illustrated as a vertical dimension in FIG. 2, and an element width 20, which is orthogonal to the element length 14 and is illustrated horizontally in FIG. 2. The element length 14 in the example structure 12 is larger than the recess depth 16 such that each electrically conductive element 4', 4" protrudes from the recess it is located in. The difference between the element length 14 and the recess depth 16 defines a protrusion length 22, in other words the extent to which each electrically conductive element 4', 4" protrudes from the recess it is located in. In the example shown in FIG. 2, the electrically conductive elements 4', 4" are rectangular in cross section, giving a constant protrusion length across the element width, and a constant element width across the protrusion length. However, in other examples, the electrically conductive elements 4', 4" may be differently shaped, provided they function to give a suitable electrical link via the sensing material for detecting an analyte.

In the example structure 12 shown in FIG. 2, the first electrically conductive element 4' comprises a first surface 24' and the second electrically conductive element 4" comprises a second surface 24"; the first surface 24' and the second surface 24" face each other and are separated by an inter-element distance 18. This inter-element distance 18 is measured in a direction orthogonal to the recess depth 16.

The sensitivity of a chemical sensing device depends on the surface area of the sensing material available for exposure to an analyte. This in turn may depend on the volume of the inter-element space available for the sensing material to occupy, which depends on the protrusion length 22, a ratio of the protrusion length 22 to the inter-element distance 18 and/or a ratio of the protrusion length 22 to the element width 20. The volume further depends on a second protrusion width, not shown, which is taken along an axis perpendicular the plane of the page of FIG. 2. The sensitivity also depends on a porosity of the sensing material.

In example structures, the at least one electrically conductive element protrudes from the at least one recess with a protrusion length 22 in a range of: 1 to 100 micro-meters; 5 to 100 micro-meters; 10 to 100 micro-meters; 15 to 100 micro-meters; 20 to 100 micro-meters; 25 to 100 micro-meters; 30 to 100 micro-meters; 35 to 100 micro-meters; 40 to 100 micro-meters; 45 to 100 micro-meters; 50 to 100 micro-meters; 55 to 100 micro-meters; 60 to 100 micro-meters; 65 to 100 micro-meters; 70 to 100 micro-meters; 75 to 100 micro-meters; 80 to 100 micro-meters; 85 to 100 micro-meters; 90 to 100 micro-meters; 95 to 100 micro-meters; 1 to 20 micro-meters; 5 to 20 micro-meters; 10 to 20 micro-meters; or 15 to 20 micro-meters. A depth of the inter-element space between the electrically conductive elements corresponds with the protrusion length. In examples, an aspect ratio of the protrusion length 22 to the element width 20 is in the range of: 0.2:1 to 20:1; 0.5:1 to 20:1; 1:1 to 20:1; 2:1 to 20:1; 3:1 to 20:1; 4:1 to 20:1; 5:1 to 20:1; 6:1 to 20:1; 7:1 to 20:1; 8:1 to 20:1; 9:1 to 20:1; 10:1 to 20:1; 11:1 to 20:1; 12:1 to 20:1; 13:1 to 20:1; 14:1 to 20:1; 15:1 to 20:1; 16:1 to 20:1; 17:1 to 20:1; 18:1 to 20:1; 19:1 to 20:1; 0.2:1 to 2:1; 0.5:1 to 2:1; or 1:1 to 2:1.

By locating the electrically conductive elements 4', 4" within the at least one recess, a high aspect ratio may be achieved, since good structural support is provided to the electrically conductive elements 4', 4" by the sides of the recess. In other words, since the surfaces of the electrically conductive elements 4', 4" within the recess are in contact with and abutting the recess sides, a base region of each element within the recess may be rigidly supported, meaning a greater protrusion length can be provided, and therefore a greater inter-element space volume for the sensing material. In example structures 12, the ratio of the element length 14 to the recess depth 16 is such that the electrically conductive elements 4', 4" are suitably structurally supported; in some examples, the ratio of the element length 14 to the recess depth 16 is 1.1:1 to 2:1.

In the example structure 12, the first surface 24' of one electrically conductive element 4' and the second surface 24" of the other electrically conductive element 4" are each planar and parallel or substantially parallel to each other. 'Substantially parallel' denotes that the plane of the first surface and the plane of the second surface are parallel to each other within a range of +1-5 degrees.

The substantially parallel nature of the surfaces 24' and 24" in this example ensures a consistent and predictable performance for the sensing device, by providing a constant inter-element distance.

In the example in which the sensing material exhibits a change in electrical conductivity when exposed to the analyte, the change in electrical conductivity produces a corresponding change in resistance. Since the magnitude of the change in resistance when the analyte comes into contact with the sensing material also depends on the separation between the electrically conductive elements, a constant separation between electrically conductive elements ensures a given change in electrically conductivity corresponds with a known change in resistance, which is consistent across the length of the electrically conductive elements. This is achieved in the example above by arranging the first 24' and second 24" surfaces of the first 4' and second 4" electrically conductive elements parallel to each other.

Examples of a method of manufacturing a structure for a chemical sensing device, such as that described above, will next be described.

In these examples, such a structure comprises at least one electrically conductive element located in, and protruding from, at least one recess, as described previously. As an overview, the method of the examples includes:

(a) providing a template comprising at least one recess having a recess depth;

(b) providing an electrically conductive material in the at least one recess; and (c) removing part of the template to decrease the recess depth of the at least one recess, thereby forming the protruding at least one electrically conductive element.

Figure 3A:
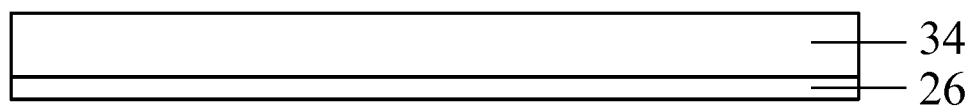
FIGS. 3a, 3b, 3c, 3d and 3e show schematically steps of an example method of manufacturing a template for a structure for a chemical sensing device.

An example method of manufacturing a template is illustrated in FIGS. 3a to 3e, using photolithography; other example methods include embossing, soft lithography, laser patterning, laser lithography and x-ray lithography In this example method, a layer of a first material 34, such as a thick film positive resist from the AZ range available from MicroChemicals GmbH, Nicolaus-Otto-Str. 39, 89079 Ulm, Germany, or a resist from the SIPR range available from Shin-Etsu MicroSi Inc., 100028 S. 51$^{st}$ Street, Phoenix, Ariz. 85044, USA, is deposited onto a substrate 26, as shown in FIG. 3a. This material may be deposited by, for example, spin coating, lamination or spray coating on the substrate 26.

Figure 3B:
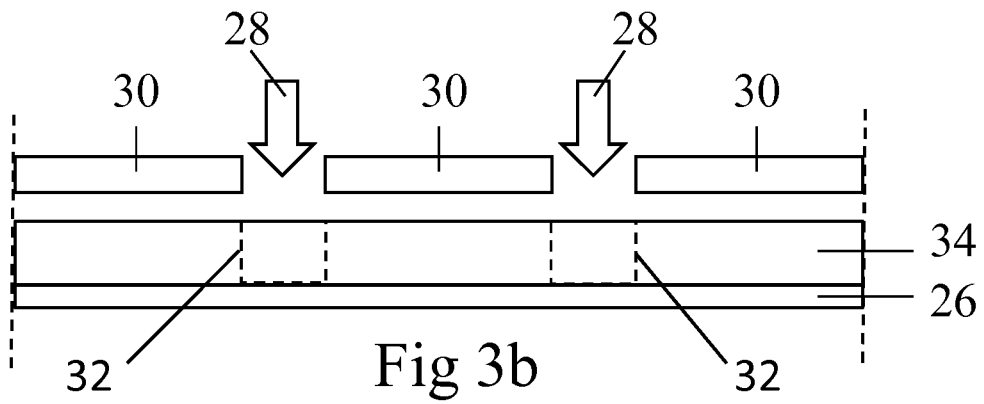

Next, as shown in FIG. 3b, masks 30 are used to cover regions of the first material to remain after a developing step (in the example that the first material 34 is to act as a positive photoresist). Thus, the mask pattern defines uncovered regions of the first material which correspond with regions to form recesses in the template, as will be explained later. Light 28 of an appropriate wavelength, for example ultraviolet light with a wavelength of 436 nano-meters, 405 nano-meters or 365 nano-meters, is applied to the uncovered regions. The exposed first material may then be removed in a development step using an appropriate solvent such as aqueous alkaline developer, for example tetramethlyammonium hydroxide (TMAH), available from Sigma Aldrich Ltd., to form at least one recess 32 indicated using dashed lines in the Figure. These recesses 32 will be used to form the at least one recess 13 of the structure described previously, as will be explained.

In other examples, a negative photoresist process may be used instead to form the recesses 32, using a mask to cover regions of the first material 34 to be removed.

Figure 3C:
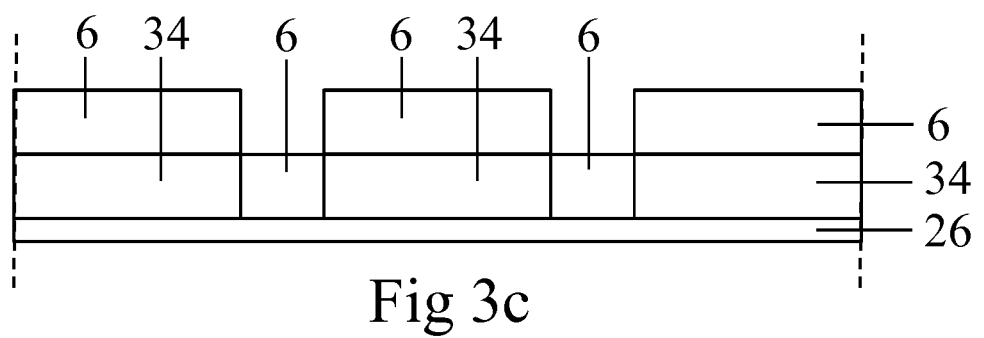

In the next step, shown in FIG. 3c, a second material 6 is deposited as a layer onto the first material 34; the second material 6 may be deposited by, for example, spin coating. In the example shown in FIG. 3c, the thickness of the layer of the second material 6 is the same as the thickness of the layer of the first material 34, however, in other examples, the first material 34 and the second material 6 may have different thicknesses. As can be seen in the Figure, a layer of the second material 6 is formed in the recesses 32 also. In this example, the second material 6 will later form the supporting material for the sensing material of the structure; hence the same reference numeral for the material is used as used previously when describing the structure 12. The second material is different from the first material in this example.

Figure 3D:
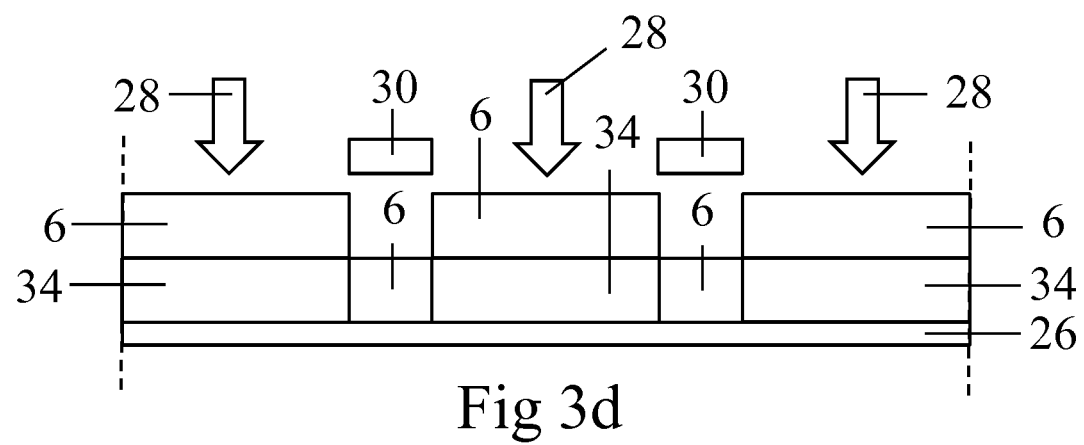

Similar steps as described using FIG. 3b are then used for the second material 6, to expose certain areas of the second material 6 to light of a given wavelength, such as ultraviolet light 28; this is shown in FIG. 3d using a mask 30 with a different pattern from that used in FIG. 3b, where the parts of the second material in the recesses 32 are covered with the mask. In this example, the second material is a negative photoresist, such as SU-8 epoxy resin for example available from MicroChemicals GmbH or from the MX series of dry film photoresists available from DuPont (UK) Ltd., Wedgwood Way, Stevenage, Hertfordshire, SG1 4QN, UK. Exposure to light of an ultraviolet wavelength, such as 365 nanometers, will harden the exposed regions of SU-8 against removal by a solvent in a developing step.

Figure 3E:
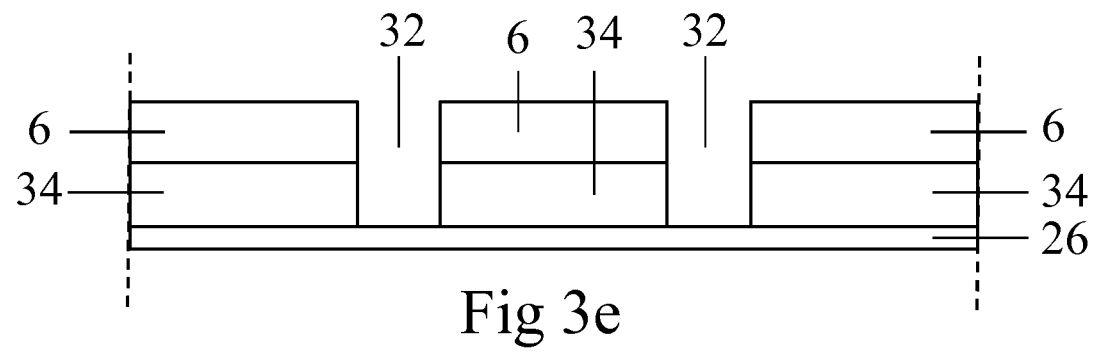

In the final step of the present example, as shown in FIG. 3e, the second material 6 in the recesses 32 has been removed in a development step by the action of an appropriate solvent, such as ethyl lactate or propylene glycol methyl ether acetate (PGMEA), available from Sigma Aldrich Ltd. or MicroChemicals GmbH to form a deeper recess 32 compared with that in FIG. 3b. In this example, both the first 34 and the second 6 material are completely removed to form at least one recess 32, leaving the substrate 26 exposed. However, in other examples, only part of the first material 34 and/or the second material 6 may be removed, leaving the substrate 26 partly or entirely covered by part of the first material 34 and/or second material 6 in the recess. Each recess 32 may be in the form of a hole, a cavity or any other opening in the first and second materials 34, 6.

The template, manufactured according to the methods described with reference to FIG. 3 for example, can then be used to manufacture a structure for a chemical sensing device. This is now described using FIGS. 4a to 4e.

Figure 4A:
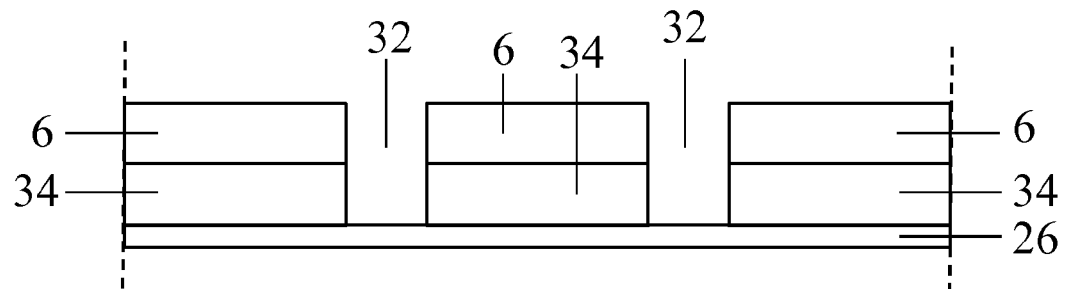
FIGS. 4a, 4b, 4c, 4d and 4e show schematically steps of a method of manufacturing a structure for a chemical sensing device according to an example.

In FIG. 4a, as an example of step (a) of the overview method given above, a template is provided which comprises at least one recess 32. In the example shown in FIG. 4a, the template is that described previously using FIGS. 3a to 3e, and therefore comprises a first layer of a first material 34 and a second layer of a second material 6. In other examples, the template may comprise a single layer of one material. In further examples, the template may comprise more than two layers of different materials. At a first side of the template there is provided the first substrate 26 in contact with the first side.

Figure 4B:
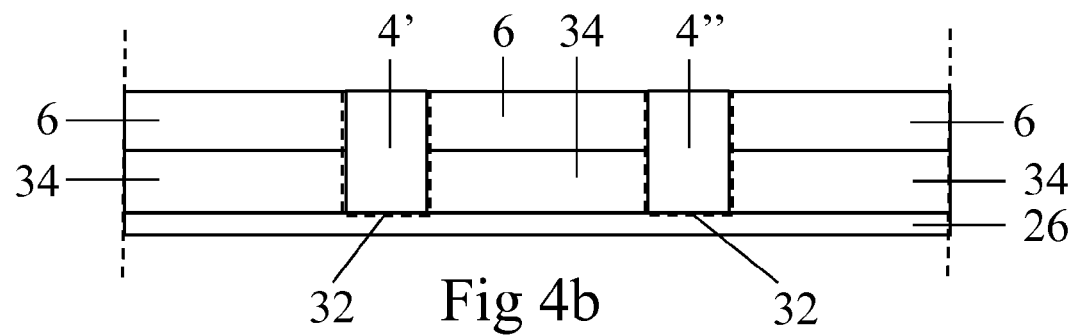

A next step is shown in FIG. 4b. In this step, as an example of step (b) of the overview method above, an electrically conductive material 4', 4" is provided in the at least one recess 32. The at least one recess 32 is now indicated in the Figure using dashed lines. In an example, this step includes using electroplating of for example nickel, but in other examples copper or other platable metals may be used. Suitable materials for electroplating are available from Enthone Inc. In the example in which electroplating is used to deposit the electrically conductive material in the at least one recess, the first substrate 26 may be electrically conductive, such as stainless steel or a stainless steel coated substrate, for providing an electric current to enable the electroplating process. As an example, electroplating may be performed by providing the at least one recess in a nickel plating bath including for example 400 milli-liters of nickel sulphate per liter, 200 milli-liters of nickel chloride per liter and 30 grammes of boric acid per liter, at a temperature of 58 degrees celsius. By applying a current of 0.5 amps to the electrically conductive first substrate 26, a plating rate of 100 amp seconds per micron may be achieved. Brighteners may optionally be added to the electroplating solution. In other examples, other methods may be used to provide the electrically conductive material 4', 4" in the at least one recess, such as electroless metal deposition.

Since the electrically conductive material will form the at least one electrically conductive element of the structure, the same reference numerals are used for the material as used previously for the electrically conductive elements.

In an example, the electrically conductive material is provided so as to fill the at least one recess 32. The filled at least one recess 32 corresponds with the filled recess 13, described later with reference to FIG. 4d. In filling the at least one recess, the electrically conductive material abuts the sides of the at least one recess. This contact between the electrically conductive material and the recess sides will provide good structural support for the electrically conductive elements of the structure being manufactured, allowing a greater aspect ratio to be provided.

Figure 4C:
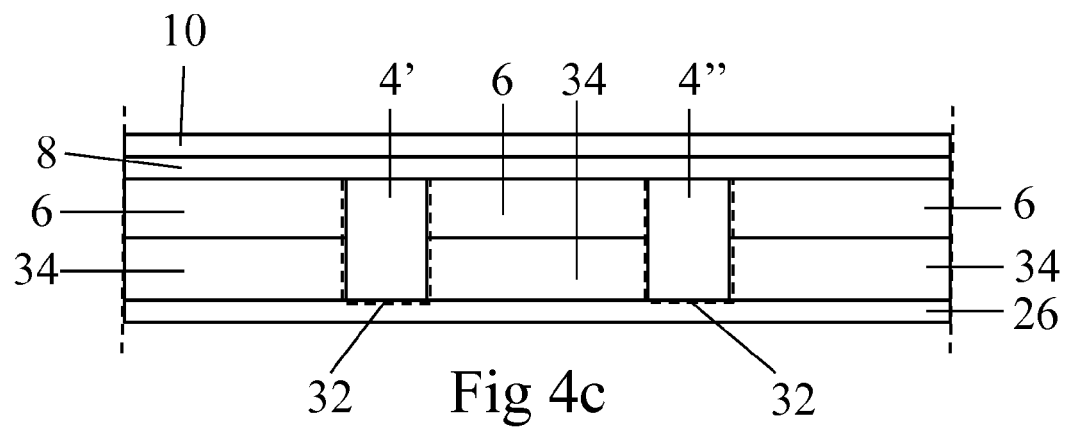

In FIG. 4c, a second substrate is placed in contact with the template and covers the at least one recess 32, for example using a lamination process. The second substrate is provided on a second side of the template, opposite the first side. In this example, the second substrate comprises an adhesive layer 8, such as Norland 81 Optical Adhesive, available from Norland Products Inc., 2540 Route 130, Suite 100, Cranbury, N.J. 08512, USA, and a further substrate layer 10, such as polyethylene terephthalate (PET), available from DuPont Teijin Films U.S. Limited Partnership, 3600 Discovery Drive, Chester, Va. 23836, USA. In other examples, the second substrate may comprise one layer, or more than two layers of different materials. Since the adhesive and PET substrate layers in the present example structure of FIG. 2 will form the substrate layers of the structure being manufactured, they are referred to using the same reference labels 8, 10 as previously used when describing the structure of FIG. 2.

Figure 4D:
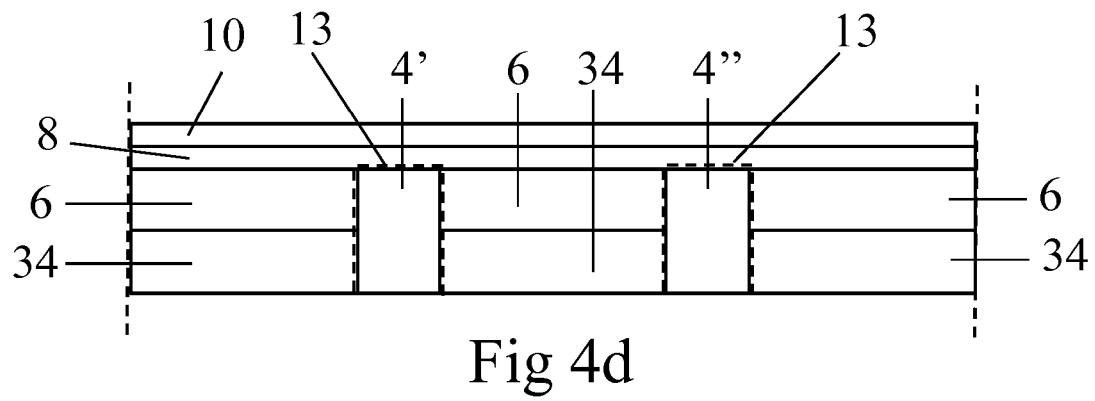

In a further step of this example, the first substrate 26 is removed, for example using a peel-off process. The resulting structure is shown in FIG. 4d. The recess 32 is now labeled with the reference numeral 13, in keeping with the reference numerals of the structure of FIG. 2.

Figure 4E:
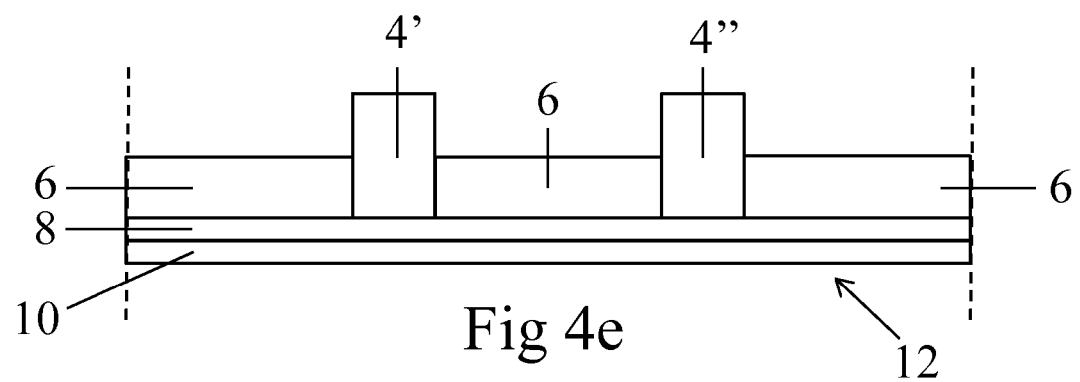

In a final step of the example, illustrated in FIG. 4e and as an example of step (c) of the overview method above, part of the template is removed, from the second side, to decrease the recess depth of the at least one recess 13, thereby forming the protruding at least one electrically conductive element 4', 4" of the structure. The structure may have been inverted before or after removing the first substrate 26, and before removing the part of the template from the second side.

In more detail, the part of the template removed is the first layer of the first material 34, leaving the layer of the second material 6 remaining. Thus, the first material 34 acts as a sacrificial material. An etching process may be used for the removal, such as oxygen plasma etching, or plasma etching with oxygen combined with tetrafluoromethane ($CF_4$). Alternatively, a solvent such as N-methyl-2-pyrrolidone (NMP), available from Sigma Aldrich Ltd. can be used to remove one layer of resist. With the first layer having a first thickness and the second layer having a second thickness, and the part of the template removed being the first layer, the decreased recess depth corresponds to the second thickness. Therefore, the protrusion length of the at least one electrically conductive element corresponds with the thickness of the first material 34. In other examples, the method may include removing part of a layer to protrude the electrically conductive elements. For example, where the template comprises a single layer, instead of the first and second layers, the method may include removing part of the single layer, leaving a remaining part in contact with the second substrate to form the at least one recess.

Once these steps have been completed, a structure for a chemical sensing device in accordance with that example described previously has been manufactured. A sensing material may then be provided in the inter-element spaces between the electrically conductive elements, for forming a chemical sensing device. The sensing material may be applied as a liquid based conductive material, using for example inkjet printing or spray coating. Controlling of a droplet size can be used to determine the network structure and/or density of the sensing material. As the skilled person will understand, electrical connections may also be formed to connect each electrically conductive element to a processing system and a measuring device, in accordance with the examples described above. These electrical connections may be formed after forming the structure, or the above method may be modified to include forming of the electrical connections, as the skilled person would understand. Examples of a structure for a chemical sensing device, and an associated method of manufacture, have been described. The structure according to the examples improves sensitivity of a chemical sensing device compared to known structures, since the method of manufacture allows electrically conductive elements with a greater protrusion length, and therefore a greater surface area for contact with a sensing material, to be formed. Moreover, the method of manufacture is more cost efficient than methods using for example isotropic silicon etching. The method in examples using the combination of photolithography and electroplating to electroplate metallic elements using a template, to form the structure, is simple and effective. Further, the method is suitable for use with flexible substrates, enabling a structure made according to examples herein to be used in a roll to roll manufacturing process for flexible electronic devices.

The preceding description has been presented only to illustrate and describe examples of the principles described. This description is not intended to be exhaustive or to limit these principles to any precise form disclosed. Many modifications and variations are possible in light of the above teaching, in accordance with the scope of the appended claims.

The invention claimed is:

1. A method of manufacturing a structure for a chemical sensing device, the structure comprising a plurality of electrically conductive elements located in, and protruding from, a plurality of recesses in the structure, the method comprising:
   providing a first substrate;
   forming a first layer on the first substrate;
   forming a second layer on the first layer;
   forming the plurality of recesses, wherein the plurality of recesses extend through the second layer and at least partially through the first layer;
   providing an electrically conductive material in the plurality of recesses;
   providing a second substrate in contact with the second layer and covering the electrically conductive material; and
   removing the first substrate and the first layer without removing the second layer to decrease the recess depth of the plurality of recesses, thereby forming said plurality of electrically conductive elements between portions of the second layer.

2. The method according to claim 1, wherein the first layer comprises a first material and the second layer comprises a second, different, material, wherein the first layer has a first thickness and the second layer has a second thickness, and wherein the decreased recess depth correspond to the second thickness.

3. The method according to claim 1, wherein providing the electrically conductive material includes using electroplating to provide the electrically conductive material in the plurality of recesses.

4. The method according to claim 1, wherein providing the electrically conductive material further comprises providing the electrically conductive material so as to fill the plurality of recesses.

5. The method according to 4, wherein the electrically conductive material is provided within the plurality of recesses so that surfaces of the electrically conductive material abut the plurality of recesses.

6. The method according to claim 1, further comprising:
   providing a sensing material on the second layer following removal of the first layer such that the sensing material is in contact with the electrically conductive material located in and protruding from a plurality of recesses.

7. The method according to claim 6, wherein providing the sensing material further comprises providing the sensing material on the second layer between the electrically conductive material extending above the second layer such that the electrically conductive material extends above the sensing material.

8. The method according to claim 6, wherein the sensing material is selected from the group consisting of: a conductive organic polymer; inorganic metal nanoparticles; inorganic oxide nanoparticles; graphene sheets coated with metal nanoparticles; carbon nanotubes coated with metal nanoparticles; nano wires and carbon black.

9. The method according to claim 6, wherein an electrical conductivity of the sensing material is to change upon exposure of the sensing material to an analyte of interest.

10. The method according to claim 1, wherein forming the plurality of recesses further comprises forming the plurality of recesses to have at least a predetermined distance between the plurality of recesses.

* * * * *